US012560575B2

(12) United States Patent
Han et al.

(10) Patent No.: US 12,560,575 B2
(45) Date of Patent: Feb. 24, 2026

(54) MICROFLUIDIC APPARATUS HAVING PORE STRUCTURE FOR DETECTING NUCLEIC ACIDS

(71) Applicant: Korea University Research and Business Foundation, Seoul (KR)

(72) Inventors: Chang Soo Han, Seoul (KR); Se Hyun Shin, Seoul (KR)

(73) Assignee: Korea University Research and Business Foundation, Seoul (KR)

( * ) Notice: Subject to any disclaimer, the term of this patent is extended or adjusted under 35 U.S.C. 154(b) by 1045 days.

(21) Appl. No.: 17/674,292

(22) Filed: Feb. 17, 2022

(65) Prior Publication Data

US 2022/0260526 A1　　Aug. 18, 2022

(30) Foreign Application Priority Data

Feb. 18, 2021　(KR) ........................ 10-2021-0022117

(51) Int. Cl.
　*G01N 27/447*　　(2006.01)
　*B01L 3/00*　　(2006.01)
　　　　(Continued)
(52) U.S. Cl.
　CPC .. *G01N 27/44791* (2013.01); *B01L 3/502715* (2013.01); *B01L 3/502753* (2013.01);
　　　　(Continued)
(58) Field of Classification Search
　None
　See application file for complete search history.

(56) References Cited

U.S. PATENT DOCUMENTS 8,524,060 B1 * 9/2013 Herr ..................... G01N 33/561
　　　　　　　　　　　　　　　　　422/82.07
2006/0194306 A1 * 8/2006 Herr ..................... G01N 27/447
　　　　　　　　　　　　　　　　　436/514
(Continued)

FOREIGN PATENT DOCUMENTS

JP　　2015-505458 A　　2/2015
KR　　10-0438828 B1　　7/2004
(Continued)

OTHER PUBLICATIONS

Extended European search report issued on Jul. 21, 2022, in counterpart European Patent Application No. 22157434.6 (8 pages in English).

*Primary Examiner* — Brian R Gordon
(74) *Attorney, Agent, or Firm* — NSIP Law

(57) ABSTRACT

The invention relates to a microfluidic apparatus for detecting nucleic acids that includes a body; a sample region provided on a first side of the body and into which a sample containing a target nucleic acid is injected; a discharge region provided on a second side of the body and spaced apart from the sample region and configured to discharge the sample; a connector that connects the sample region and the discharge region to each other to provide a flow path through which the sample flows; a pore region provided inside the connector, having at least one pore, and configured to induce clogging of the pore; and an electrode region determining whether the target nucleic acid is amplified, wherein probe linkers that bind to and amplify the target nucleic acid are provided in the pore region, and the electrode region measures a degree of clogging of the at least one pore.

16 Claims, 4 Drawing Sheets

1

(51) Int. Cl.
    *C12Q 1/6825*     (2018.01)
    *C12Q 1/6876*     (2018.01)

(52) U.S. Cl.
    CPC ......... *C12Q 1/6825* (2013.01); *C12Q 1/6876* (2013.01); *B01L 2300/0645* (2013.01); *B01L 2300/0819* (2013.01)

(56) References Cited

U.S. PATENT DOCUMENTS

| | | | |
|---|---|---|---|
| 2013/0186757 A1* | 7/2013 | Reinhart | C07D 235/24 |
| | | | 204/603 |
| 2014/0374255 A1* | 12/2014 | Hongo | G01N 15/12 |
| | | | 204/627 |
| 2015/0153302 A1* | 6/2015 | Davis | G01N 27/3278 |
| | | | 204/403.08 |
| 2015/0377830 A1* | 12/2015 | Baldauf | G01N 33/48721 |
| | | | 204/601 |
| 2017/0097332 A1 | 4/2017 | Paik et al. | |
| 2018/0044725 A1* | 2/2018 | Kokoris | G01N 27/44791 |
| 2018/0275088 A1* | 9/2018 | Huff | B01L 3/50273 |
| 2018/0356412 A1* | 12/2018 | Lindsay | C12M 1/34 |
| 2018/0362594 A1* | 12/2018 | Cech | C12N 9/1252 |
| 2019/0113507 A1 | 4/2019 | Shin | |
| 2020/0024654 A1* | 1/2020 | Heron | C12Q 1/6876 |
| 2021/0322976 A1* | 10/2021 | Ng Pitti | B01L 3/502707 |

FOREIGN PATENT DOCUMENTS

| | | |
|---|---|---|
| KR | 10-1799192 B1 | 11/2017 |
| WO | WO 2015/196148 A1 | 12/2015 |

* cited by examiner

[FIG. 1]
1
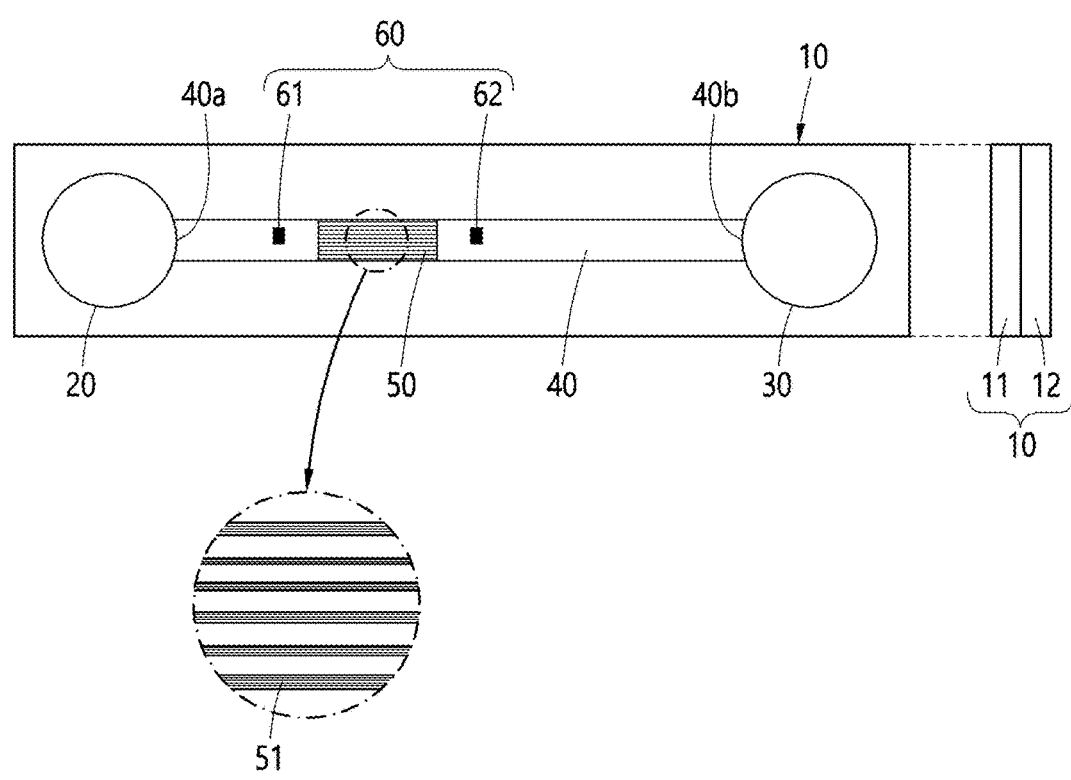
[FIG. 2]
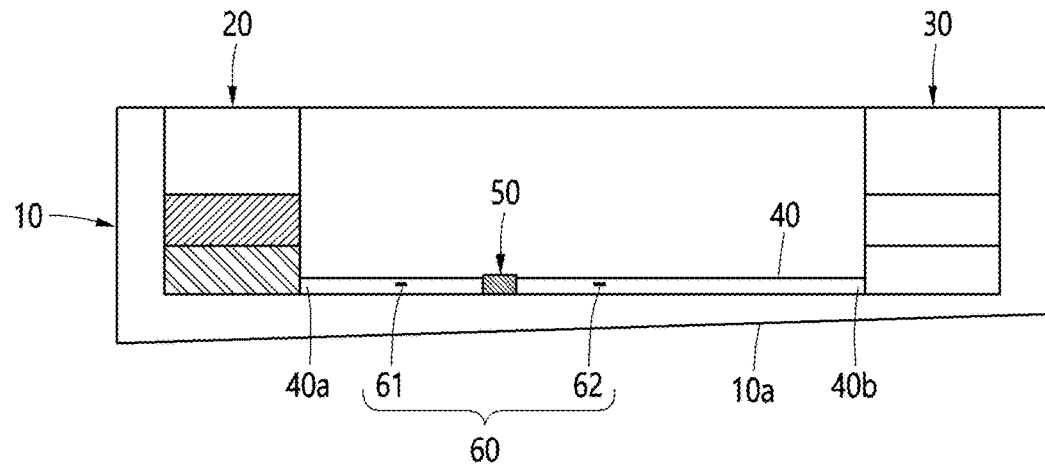

[FIG. 3]
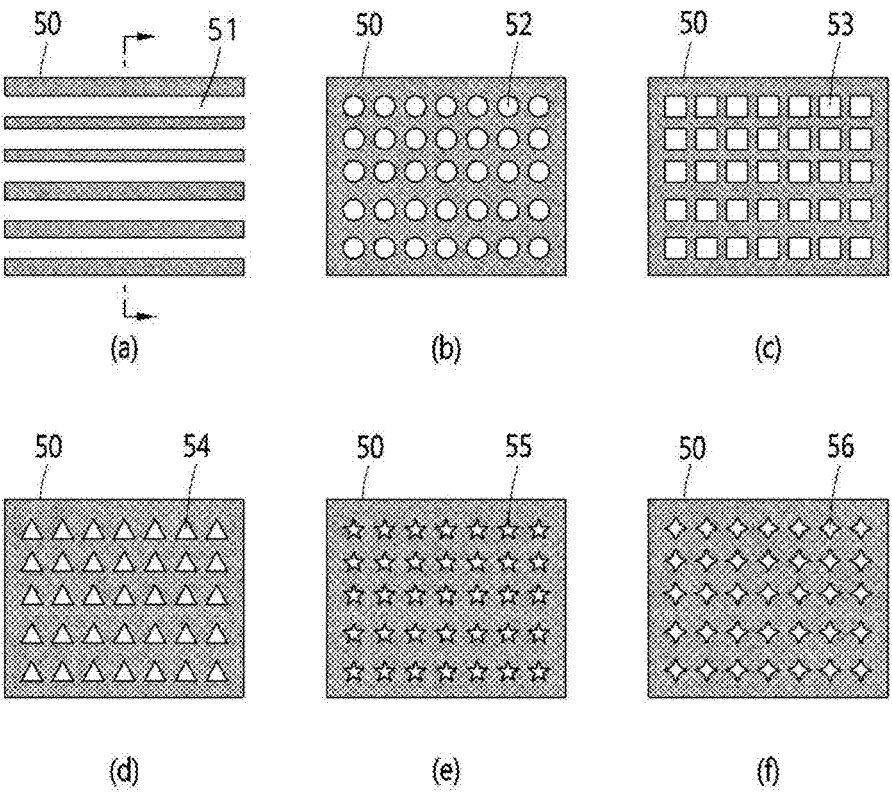
(a)                  (b)                  (c)
(d)                  (e)                  (f)
[FIG. 4]
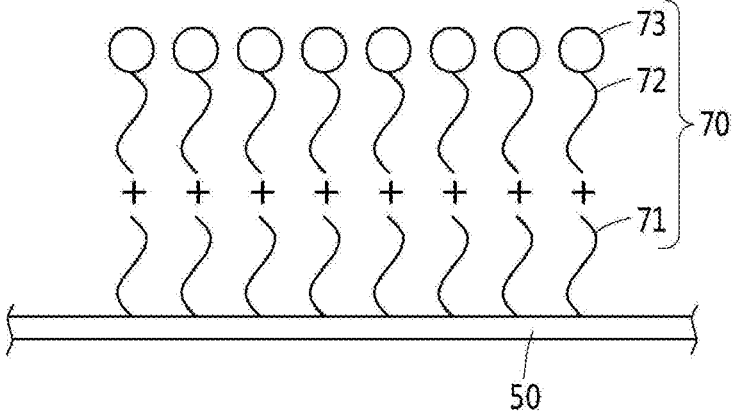

[FIG. 5]
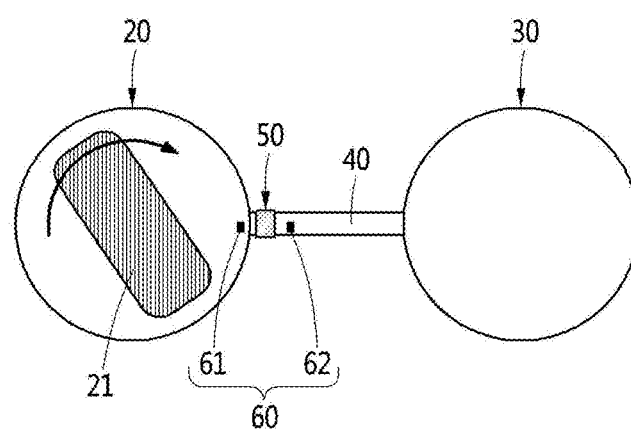
[FIG. 6]
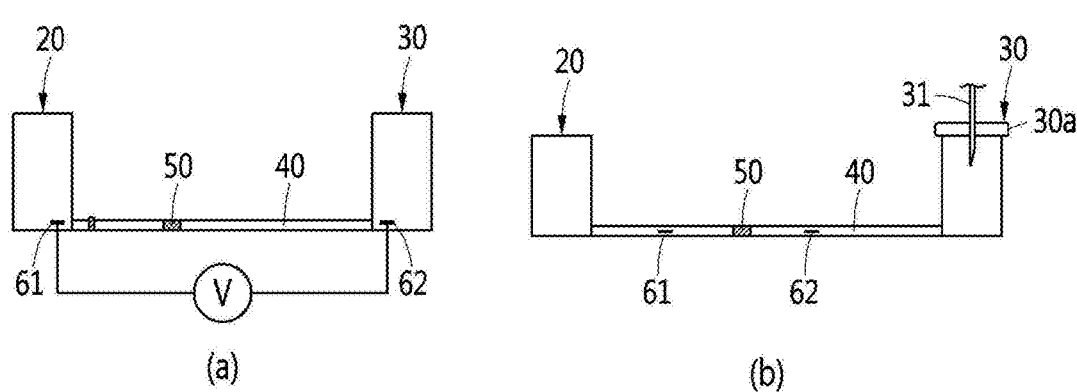
(a)                                              (b)

[FIG. 7]
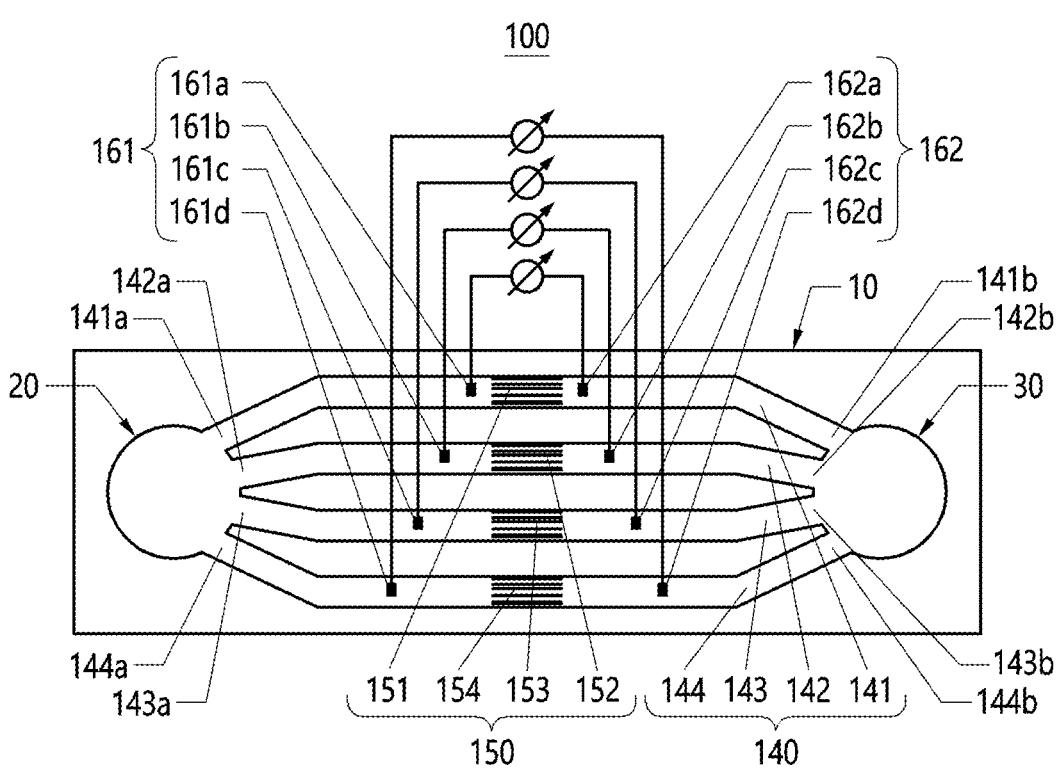

MICROFLUIDIC APPARATUS HAVING PORE STRUCTURE FOR DETECTING NUCLEIC ACIDS

CROSS-REFERENCE TO RELATED APPLICATION

This application claims priority to Korean Patent Application No. 10-2021-0022117, filed on Feb. 18, 2021 in the Korean Intellectual Property Office, the disclosure of which is incorporated herein by reference.

BACKGROUND OF THE DISCLOSURE

Field of the Disclosure

The present disclosure relates to a microfluidic apparatus having a pore structure for detecting nucleic acids, and more particularly, to a microfluidic apparatus having a pore structure for detecting nucleic acids that is capable of increasing accuracy with a simple structure when detecting a target nucleic acid such as RNA.

Description of the Related Art

Efficient amplification of a target nucleic acid such as a virus is a very important factor in nucleic acid detection, DNA sequencing, cloning, and the like. Methods for amplifying nucleic acids include polymerase chain reaction (PCR), ligase chain reaction (LCR), self-sustained sequence replication (SSR), nucleic acid sequence based amplification (NASBA), and strand displacement amplification (SDA).

These methods for nucleic acid amplification are somewhat inaccurate in quantitative measurement and require expensive equipment. In particular, when more than one type of target nucleic acid is analyzed simultaneously, the accuracy is further lowered. To solve the limitations of these nucleic acid amplification methods, isothermal nucleic acid amplification methods have been used in recent years. In particular, among isothermal reaction methods, many researches have been made on a rolling circle amplification (RCA) method capable of amplifying a target nucleic acid in an isothermal state without temperature changes during PCR amplification.

As described above, in recent years, to overcome the limitations in amplifying a target nucleic acid, various studies have been continuously conducted.

RELATED ART DOCUMENTS

Patent Documents (Patent Document 1) Korean Patent No. 10-0438828
(Patent Document 2) Japanese Patent Application Publication No. 2015-505458

SUMMARY OF THE DISCLOSURE

Therefore, the present disclosure has been made in view of the above problems, and it is an object of the present disclosure to provide a microfluidic apparatus having a pore structure for detecting nucleic acids that has high accuracy with a simple structure when detecting a target nucleic acid.

In accordance with one aspect of the present disclosure, provided is a microfluidic apparatus for detecting nucleic acids including a body; a sample region provided on one side of the body and into which a sample containing a target nucleic acid to be detected is injected; a discharge region provided on the other side of the body so as to be spaced apart from the sample region and configured to discharge the sample in which the target nucleic acid has been detected; a connector configured to connect the sample region and the discharge region to each other to provide a flow path through which the sample flows; a pore region provided inside the connector, having at least one pore, and configured to induce clogging of the pore through amplification of the target nucleic acid contained in the sample; and an electrode region for determining whether the target nucleic acid is amplified by measuring a change in an electrical signal of the sample passing through the pore region, wherein probe linkers that bind to and amplify the target nucleic acid are provided in the pore region, and the electrode region measures a degree of clogging of the at least one pore by binding between the target nucleic acid and the probe linkers to detect the target nucleic acid.

In addition, the body may have a chip shape including upper and lower bodies that are laminated on each other.

In addition, the sample region and the discharge region may each have a chamber shape, and the connector may include a connecting conduit having an inlet connected to the sample region and an outlet connected to the discharge region.

In addition, the pore region may be provided inside the connector so that the pore region is closer to the sample region than the discharge region.

In addition, the at least one pore may be provided so as to penetrate in a flow direction of the sample from the sample region toward the discharge region, and a cross-section of the at least one pore may have various shapes.

In addition, the probe linker may include a coating member applied to a surface of the pore region, a primer fixed to the coating member, and a template bound to the primer.

In addition, a stirrer for stirring the sample may be provided inside the sample region; and the stirrer may stir the sample for a preset stirring time, and then may discharge the sample to the connector, wherein the stirring time is variable.

In addition, a heating means for amplifying a binding force between the target nucleic acid and the probe linkers by heating the sample for a preset heating time may be provided inside the sample region.

In addition, the electrode region may include a first electrode provided in the connector to be positioned between the sample region and the pore region; and a second electrode provided in the connector to be positioned between the pore region and the discharge region, wherein the first and second electrodes are used to measure the target nucleic acid detected by a degree of clogging of the at least one pore by measuring a signal change by the sample passing through the pore region.

In addition, using an electrophoretic force by the first and second electrodes, the sample may flow from the sample region to the discharge region.

In addition, the first and second electrodes may be provided on one side of an inner surface of the connector, and a direct current voltage or an alternating current voltage may be applied to between the first and second electrodes.

In addition, an additive for increasing fluidity of the sample may be added to the sample region, and the additive may include ions that increase conductivity.

In addition, the sample may flow from the sample region to the discharge region by a flow force generated by at least one of negative pressure between the sample region and the discharge region, gravity according to an inclined shape of the body inclined from the sample region toward the discharge region, and a water head difference between the sample region containing the sample and the hollowed discharge region.

In addition, oil may be injected into the sample injected into the sample region to block an upper surface of the sample from outside to increase the gravity or the water head difference.

In addition, the connector may include a plurality of connecting conduits each independently connecting the sample region and the discharge region, and the pore regions may include a plurality of pore members each having the at least one pore, and the pore regions may be provided in plural and may each be independently provided in the connecting conduits.

In addition, the probe linkers provided in each of the pore members may be different or the same, and the size of the at least one pore provided in each of the pore members may be different or the same.

In addition, the probe linkers may not be provided on any one of the pore members, and the pore member may be used as a negative reference channel in which the at least one pore is always open regardless of amplification of a target nucleic acid, or the probe linkers may be formed on any one of the pore members so that amplification occurs regardless of presence or absence of the target nucleic acid, and the pore member may be used as a positive reference channel.

In addition, the electrode region may include at least one first electrode provided at an inlet of each of the connecting conduits respectively connected to the pore members so as to be respectively positioned between the sample region and the pore members; and a plurality of second electrodes provided at an outlet of each of the connecting conduits respectively connected to the pore members so as to be respectively positioned between the pore members and the discharge region.

In accordance with another aspect of the present disclosure, provided is a microfluidic apparatus for detecting nucleic acids including a sample region into which a sample containing a target nucleic acid to be detected is injected; a discharge region disposed to be spaced apart from the sample region and configured to discharge the sample; a connector providing a sample flow path between the sample region and the discharge region; a pore region having at least one pore, provided in the flow path, and provided with probe linkers that bind to and amplify the target nucleic acid to induce clogging of the pore; and an electrode region for measuring whether the target nucleic acid is amplified through the pore region by measuring an electrical signal change of the sample before and after passing through the pore region.

In addition, the microfluidic apparatus may include a chip-shaped body in which the sample region, the discharge region, the connector, the pore region, and the electrode region are provided, wherein the sample region and the discharge region are formed in a chamber shape.

In addition, the pore region may be provided inside the connector so that the pore region is closer to the sample region than the discharge region.

In addition, the pore of the pore region may be provided so as to penetrate in a flow direction of the sample from the sample region toward the discharge region, and a cross-section of the pore may have various shapes.

In addition, the probe linker may include a coating member applied to a surface of the pore region, a primer fixed to the coating member, and a template bound to the primer.

In addition, a stirrer for stirring the sample may be provided inside the sample region; and the stirrer may stir the sample for a preset stirring time, and then may discharge the sample to the connector, wherein the stirring time is variable.

In addition, a heating means for amplifying a binding force between the target nucleic acid and the probe linkers by heating the sample for a preset heating time may be provided inside the sample region.

In addition, the electrode region may include a first electrode provided in the connector to be positioned between the sample region and the pore region; and a second electrode provided in the connector to be positioned between the pore region and the discharge region, wherein the first and second electrodes measure the target nucleic acid detected by a degree of clogging of the at least one pore by measuring a signal change by the sample passing through the pore region.

In addition, using an electrophoretic force by the first and second electrodes, the sample may flow from the sample region to the discharge region.

In addition, the first and second electrodes may be provided on one side of an inner surface of the connector, and a direct current voltage or an alternating current voltage may be applied to the first and second electrodes.

In addition, an additive for increasing fluidity of the sample may be added to the sample region, and the additive may include ions that increase conductivity.

In addition, the sample may flow from the sample region to the discharge region by a flow force generated by at least one of negative pressure between the sample region and the discharge region, gravity according to an inclined shape of the body inclined from the sample region toward the discharge region, and a water head difference between the sample region containing the sample and the hollowed discharge region; and oil may be injected into the sample injected into the sample region to block an upper surface of the sample from outside to increase the gravity or the water head difference.

In addition, the connector may include a plurality of connecting conduits each independently connecting the sample region and the discharge region, and the pore regions may include a plurality of pore member each having the at least one pore, and the pore regions may be provided in plural and may each be independently provided in the connecting conduits.

In addition, the probe linkers provided in the pore members may be different or the same, and the size of the at least one pore provided in the pore members may be different or the same.

In addition, the probe linkers may not be provided on any one of the pore members, and the pore member may be used as a negative reference channel in which the at least one pore is always open regardless of amplification of a target nucleic acid, or the probe linkers may be formed on any one of the pore members so that amplification occurs regardless of presence or absence of the target nucleic acid, and the pore member may be used as a positive reference channel.

In addition, the electrode region may include at least one first electrode provided at an inlet of the connector connected to the sample region; and a plurality of second electrodes respectively provided in the connecting conduits so as to be positioned between the pore region and the discharge region.

BRIEF DESCRIPTION OF THE DRAWINGS

The above and other objects, features and other advantages of the present disclosure will be more clearly understood from the following detailed description taken in conjunction with the accompanying drawings, in which:

FIG. 1 schematically illustrates a microfluidic apparatus having a pore structure for detecting nucleic acids according to a preferred embodiment of the present disclosure;

FIG. 2 is a schematic cross-sectional view of the microfluidic apparatus having a pore structure for detecting nucleic acids shown in FIG. 1;

FIG. 3 schematically illustrates various embodiments of a pore region included in the microfluidic apparatus having a pore structure for detecting nucleic acids shown in FIG. 1;

FIG. 4 schematically illustrates a pore region included in the microfluidic apparatus having a pore structure for detecting nucleic acids shown in FIG. 1;

FIG. 5 schematically illustrates a modification example of a sample region included in the microfluidic apparatus having a pore structure for detecting nucleic acids shown in FIG. 1;

FIG. 6 includes drawings for explaining application of a sample flow force in the microfluidic apparatus having a pore structure for detecting nucleic acids shown in FIG. 1; and FIG. 7 schematically illustrates a microfluidic apparatus having a pore structure for detecting nucleic acids according to another embodiment of the present disclosure.

DETAILED DESCRIPTION OF THE DISCLOSURE

Hereinafter, preferred embodiments of the present disclosure will be described with reference to the accompanying drawings. However, the spirit of the present disclosure is not limited to the embodiments, and the spirit of the present disclosure may be proposed differently by adding, changing, and deleting the elements constituting the embodiments, which is also within the spirit of the present disclosure.

FIG. 1 schematically illustrates a microfluidic apparatus 1 having a pore structure for detecting nucleic acids according to a preferred embodiment of the present disclosure, and FIG. 2 is a schematic cross-sectional view of the microfluidic apparatus 1 having a pore structure for detecting nucleic acids.

Referring to FIG. 1, the microfluidic apparatus 1 having a pore structure for detecting nucleic acids of the present disclosure includes a body 10, a sample region 20, a discharge region 30, a connector 40, a pore region 50, and an electrode region 60.

As shown in FIG. 1, the body 10 is provided in a chip shape including an upper body 11 and a lower body 12. In the body 10, by mutual coupling of the upper body 11 and the lower body 12, the sample region 20, the discharge region 30, the connector 40, and the pore region 50 to be described later may be provided.

The sample region 20 is provided on one side of the body 10, and a conductive sample fluid containing a target nucleic acid to be detected is injected thereto. As shown in FIG. 2, the sample region 20 is provided as a sample chamber having a predetermined height inside the body 10, and a sample is injected thereto.

The discharge region 30 is provided on the other side of the body 10 so as to be spaced apart from the sample region 20. As shown in FIG. 2, the discharge region 30 may be provided as a discharge chamber having a predetermined height inside the body 10.

The connector 40 is configured so that the sample region 20 and the discharge region 30 are connected to each other. As shown in FIG. 2, the connector 40 may form a sample flow path between the sample region 20 and the discharge region 30 provided as a kind of chamber, and may be provided as a connecting conduit for connecting the sample region 20 and the discharge region 30 to each other. The connector 40 may be provided in the body 10 in the form of a microchannel for mutually communicating the sample region 20 and the discharge region 30, and may include an inlet 40a connected to the sample region 20 and an outlet 40b connected to the discharge region 30.

The pore region 50 is provided in the connector 40, and has one or more pores 51 to induce clogging of the pores 51 through amplification of a target nucleic acid from a sample. The pore region 50 is provided in the connector 40 to be biased toward the sample region 20, which is more advantageous for detecting a target nucleic acid. That is, the pore region 50 is provided on the inlet side of the connector 40. With this configuration, a sample accommodated in the sample region 20 passes through the pore region 50 provided on the inlet side of the connector 40, and at this time, bubbling of the sample generated in the process of passing the pore region 50 may be prevented.

For reference, when the flow rate of a sample passing through the connector 40 is high, bubbles may be generated, and these bubbles may impede sample flow. To prevent bubbles from occurring during sample flow, when the flow pressure of a sample is reduced, reproducibility may be reduced when detection of a target nucleic acid is repeated, and frequent changes in flow pressure may require control, which may limit detection. Accordingly, in the microfluidic apparatus 1 for detecting nucleic acids described in the present disclosure, by providing the pore region 50 on the inlet side of the connector 40 connected to the sample region 20, degradation of detection power due to generation of bubbles during sample flow may be prevented.

In addition, as shown in (a) of FIG. 3, the pore region 50 may be provided in the form of a pore membrane. In the pore region 50, the pores 51 may be provided in plural. Here, as shown in FIGS. 3B to 3F, the pores 51 may be formed in one or more complex shapes, and may be formed to penetrate the pore region 50 in the direction of sample flow.

For example, in the cross section of the pore region 50, round pores 52 ((b) of FIG. 3), square pores 53 ((c) of FIG. 3), triangular pores 54 ((d) of FIG. 3), star-shaped pores 55 ((e) of FIG. 3), and spherical pores 56 ((f) of FIG. 3) may be provided. That is, the cross-sections of the one or more pores 52 to 56 may be formed in various shapes, including a circular shape.

The pores 51 are micropores penetrating the pore region 50 in the flow direction of a sample. Even when the pore region 50 for nucleic acid detection is installed to block the entrance of the connector 40, a sample may flow through the pores 51. For reference, as the size of the pores 51 increases, a sample flows more easily. Under the condition that the volume of the pores 51 is the same, as the surface area of the pores 51 increases, nucleic acid detection in a flow sample is easier.

In addition, as shown in FIG. 4, probe linkers 70 are provided in the pore region 50. The probe linkers 70 include coating members 71, primers 72, and templates 73.

The surface of the pore region 50 is coated with the coating members 71. The coating members 71 are made of a material to which the primers 72 may be attached and fixed. For example, the coating members 71 may be made of a material including a carboxyl group or an amine group, and the surface of the pore region 50 may be coated with the coating members 71. More specifically, the coating members 71 may include one or more selected from the group consisting of 5-hydroxydopamine (5-OHDA) hydrochloric acid, norepinephrine, epinephrine, pyrogallolamine, 3,4-Di-hydroxyphenylalanine (DOPA), catechin, tannins, pyrogallol, pyrocatechol, heparin-catechol, chitosan-cat-echol, polyethylene glycol-catechol, polyethylenimine-cat-echol, polymethyl methacrylate-catechol, hyaluronic acid-catechol, polylysine-catechol, and polylysine.

The primers 72 are fixed to the coating members 71. The primers 72 are provided between the templates 73 to be described later and the coating members 71, and are bound to the templates 73. Here, the ends of the primers 72 may be modified with one or more selected from the group consisting of a thiol, an amine, a hydroxyl group, a carboxyl group, isothiocyanate, N-hydroxysulfosuccinimide (NHS) ester, an aldehyde, an epoxide, a carbonate, hydroxybenzotriazole (HOBt) ester, glutaraldehyde, a carbamate, imidazole car-bamate, maleimide, aziridine, a sulfone, vinylsulfone, hydrazine, phenyl azide, benzophenone, anthraquinone, and a diene group.

The templates 73 complementarily bind to the primers 72. Although not shown in detail, each of the templates 73 may include first binding regions complementary to a target nucleic acid included in a sample, a second binding region complementary to the primer 72, and third binding regions complementary to the inside of the template 73 to maintain a dumbbell shape. Here, the first binding regions of the template 73 is formed separately at both ends of the template 73, and the second binding region is formed between the third binding regions formed separately.

For reference, the configuration of the template 73 having the first to third binding regions is only an example, and the present disclosure is not limited thereto.

The probe linkers 70 having such a configuration are coupled to a target nucleic acid included in a sample, the target nucleic acid is amplified, and the amplified target nucleic acids are attached to the probe linkers 70 to form a large-sized hydrogel. At this time, the large-sized hydrogel may block the pores 51 penetrating through the pore region 50. That is, by amplification through complementary bind-ing between the probe linkers 70 and a target nucleic acid, the pores 51 of the pore region 50 may be blocked, or the passage area through the pores 51 may be reduced. A target nucleic acid is detected by measuring a change in fluid resistance or impedance between both ends of the pore region 50 due to an internal change of the pores 51. As a result, the target nucleic acid is amplified through comple-mentary binding between the probe linkers 70 and the target nucleic acid included in the sample, so that the target nucleic acid is detected.

Here, the pores 51 are formed in a size suitable for applying the probe linkers 70, and as the size of the pores 51 decreases, the clogging speed of the pores 51 increases, which is an advantage. On the other hand, as the size of the pores 51 decreases, the flow resistance of a sample is increased, and it is difficult to apply the probe linkers 70 inside the pores 51. Accordingly, by selecting the size of the pores 51 in consideration of the flow conditions of a sample, nucleic acids included in the sample may be detected under various conditions.

In addition, as shown in FIG. 5, the microfluidic apparatus 1 for detecting nucleic acids of the present disclosure may further include a stirrer 21. The stirrer 21 stirs a sample inside the sample region 20, thereby bringing the stirred sample into contact with the pore region 50 installed close to the inlet of the connector 40 connected to the sample region 20. Accordingly, during the stirring process by the stirrer 21, the probability that a target nucleic acid in the sample is complementary to the probe linkers 70 formed in the pore region 50 increases.

For reference, the stirrer 21 stirs a sample in the sample region 20 for a preset stirring time and then discharges the sample to the connector 40, thereby allowing the sample to flow along the connector 40. Here, the stirring time may be set between approximately 5 minutes and 30 minutes, and the stirring time is preferably set in consideration of time required for complementary binding between the probe linkers 70 and a target nucleic acid, test time, and the like.

In addition, although not shown in detail, a heating means (not shown) for heating a sample injected into the sample region 20 to a preset temperature range may be included. Here, the heating temperature range of the heating means (not shown) is set to an optimum reaction temperature for an amplification process by complementary binding between the probe linkers 70 and a target nucleic acid, i.e., passive cutaneous anaphylaxis reaction (PCA). In this embodiment, the heating temperature range is approximately 30 to 37° C.

In addition to setting the heating temperature of the heating means (not shown), the stirring time of the stirrer 21 may be set within the range of 5 to 30 minutes. Due to the configuration of the stirrer 21 and the heating means (not shown), a sample heated and stirred inside the sample region 20 is sufficiently coupled to the probe linkers 70 formed on the surface of the pore region 50.

Accordingly, when a sample discharged from the sample region 20 passes through the pores 51 of the pore region 50, the flow rate of the sample may be increased. As a result, a target nucleic acid rapidly binds to the probe linkers 70, and clogging of the pores 51 is induced, thereby reducing detection time. In addition, before the sample passes through the pores 51, since a target nucleic acid included in the sample and the probe linkers 70 are in combined state in advance, occurrence of bubbles may be prevented when the sample flows through the pores 51.

The electrode region 60 measures an electrical signal change in a sample passing through the pore region 50 to detect target nucleic acids amplified in the pore region 50. That is, the electrode region 60 measures the electrical resistance or impedance of a conductive sample fluid before and after the pore region 50, thereby measuring a minute electrical change signal according to the degree of clogging of the pores 51.

The electrode region 60 includes first and second elec-trodes 61 and 62 provided in the connector 40 to face each other with the pore region 50 interposed therebetween. Since the electrode region 60 includes the first and second elec-trodes 61 and 62 facing each other with the pore region 50 interposed therebetween, the electrode region 60 may mea-sure a change in the flow amount of a sample passing through the pore region 50. The first and second electrodes 61 and 62 measure the flow amount of a sample flowing from the sample region 20 to the connector 40 and the flow amount of the sample flowing from the connector 40 to the discharge region 30 as relative signal changes according to electrical changes, thereby detecting nucleic acids.

In addition, the first and second electrodes 61 and 62 of the electrode region 60 are disposed so as to be in contact with a sample flowing in the connector 40. The first and second electrodes 61 and 62 measure electrical signals and generate a flow force that causes a sample to flow by means of an electrophoretic force. That is, in the electrode region 60 according to present embodiment, a voltage is applied to the first and second electrodes 61 and 62 respectively provided on the sample region 20 and the discharge region 30 to detect a target nucleic acid and generate a sample flow force by an electrophoretic force. Since the electrode region 60 including the first and second electrodes 61 and 62 use an electrophoretic force, compared to sample flow by the pressure difference between the sample region 20 and the discharge region 30, there is an advantage in that a compact design is possible.

In addition, to improve a flow force by electrophoresis, it is advantageous that the conductivity of a sample injected into the sample region 20 is improved. By adding an additive containing ions having higher conductivity than water to the inside of the sample region 20, the conductivity of a sample may be increased to increase a flow force. The additive is preferably selected so as not to affect nucleic acid amplification by the primers 72 and the templates 73 of the probe linkers 70. In this embodiment, to increase the electrical conductivity of a sample, ions including at least one of KCl, NaCl, and $CaCl_3$) are used.

Here, the installation positions of the first and second electrodes 61 and 62 of the electrode region 60 are not limited to the positions shown in FIG. 1. For example, as shown in FIG. 6A, a modification example in which the first and second electrodes 61 and 62 are respectively provided in the sample region 20 and the discharge region 30 is also possible.

In addition, the present disclosure is not limited to generation of a sample flow force using an electrophoretic force by the electrode region 60, and various means for generating a flow force may be applied. For example, as shown in FIG. 6B, in a state in which the discharge region 30 is closed by a stopper 30a, while the stirrer 21 stirs a sample in the sample region 20, when an exhaust line 31 is formed using an injection needle, a water head difference is generated between the hollowed discharge region 30 and the sample region 20. Accordingly, a modification example in which a sample in the sample region 20 passes through the pores 51 of the pore region 50 and flows along the connector 40 to be introduced into the discharge region 30 is also possible.

As described above, in the present embodiment, detection of a target nucleic acid using the electrode region 60 and a sample flow force by an electrophoretic force are exemplified, but the present disclosure is not limited thereto. That is, a flow force that causes a sample to flow along the connector 40 may be generated by at least one of the negative pressure between the sample region 20 and the discharge region, gravity according to the inclined shape of the body 10 inclined from the sample region 20 toward the discharge region 30, and the water head difference between the sample region 20 containing a sample and the hollowed discharge region 30.

Here, when the electrode region 60 generates a flow force by using gravity or a water head difference, oil that does not mix with a sample may be injected into the sample region 20 after injection of the sample. The oil blocks the upper surface of a sample injected into the sample region 20 from the outside, thereby increasing gravity or a water head difference for the flow force of the electrode region 60 responsible for sample flowing along the connector 40.

In addition, when the electrode region 60 generates a sample flow force by using an electrophoretic force, the voltage directions of the first and second electrodes 61 and 62 may be switched by repeated passage of a sample through the pore region 50. Switching of voltage directions provides an environment in which the frequency of contact between the probe linkers 70 provided inside the pores 51 and a target nucleic acid is increased, so that clogging of the pores 51 may be quickly induced. The voltage applied to the first and second electrodes 61 and 62 may be a direct current voltage or alternating current voltage. Preferably, an alternating current voltage with a low frequency of 10 Hz or less is used.

The nucleic acid detection operation of the microfluidic apparatus 1 for detecting nucleic acids of the present disclosure having the above configuration is summarized as follows with reference to FIG. 1.

When a sample is injected into the sample region 20, the sample is discharged toward the discharge region 30 by an electrophoretic force by the first and second electrodes 61 and 62 of the electrode region 60. At this time, a stirrer 21 may be provided inside the sample region 20 to stir the sample for a preset stirring time, and the sample may be heated by a heating means (not shown).

The sample discharged from the sample region 20 is introduced into the inlet of the connector 40, and passes through the pore region 50 provided in the connector 40. Here, since the probe linkers 70 are formed in the pore region 50, a target nucleic acid included in the sample is amplified by binding to the probe linkers 70, and the pores 51 formed through the pore region 50 in the flow direction of the sample are clogged by the amplified target nucleic acids. Accordingly, the electrode region 60 detects a target nucleic acid by measuring a change in fluid resistance or impedance between both ends of the pore region 50 according to a size change such as clogging of the pores 51. The sample passing through the pore region 50 is introduced into the discharge region 30 and discarded.

FIG. 7 schematically illustrates a microfluidic apparatus 100 for detecting nucleic acids according to another embodiment of the present disclosure.

Referring to FIG. 7, the microfluidic apparatus 100 according to another embodiment includes a body 10, a sample region 20, a discharge region 30, connectors 140, pore regions 150, and electrode regions 160. Here, the configuration of the body 10, the sample region 20, and the discharge region 30 is similar to the above-described exemplary embodiment, and thus the same reference numerals as those of the exemplary embodiment are assigned and detailed descriptions thereof will be omitted.

The connectors 140 according to another embodiment include a plurality of connecting conduits 141 to 144 to independently connect the sample region 20 and the discharge region 30, respectively. Hereinafter, for convenience of explanation, the connectors 140 are exemplified as including four connecting conduits 141 to 144. The four connecting conduits 141 to 144 are described as first to fourth connecting conduits 141 to 144 provided in the body 10 to independently connect the sample region 20 and the discharge region 30. For reference, the number of the connecting conduits 141 to 144 is only an example, and is not limited to the illustrated example.

The pore regions 150 are provided in the first to fourth connecting conduits 141 to 144, respectively, and detect a target nucleic acid from a sample. For this function, the pore regions 150 include first to fourth pore members 151 to 154 corresponding to the first to fourth connecting conduits 141 to 144, respectively. Here, the first to fourth pore members 151 to 154 are provided to be parallel to each other.

With this configuration, the first pore member 151 provided in the first connecting conduit 141 detects a target nucleic acid from a sample using the probe linkers 70 (see FIG. 4) formed on the surface thereof, and the second pore member 152 provided in the second connecting conduit 142 detects a target nucleic acid using the probe linkers 70. Likewise, the probe linkers 70 formed on each of the third and fourth pore members 153 and 154 provided in the third and fourth connecting conduits 143 and 144, respectively, detect a target nucleic acid from a sample.

In addition, the probe linkers 70 formed on the first to fourth pore members 151 to 154 may be provided in different types, and may be complementarily bound to different types of target nucleic acids. Accordingly, the first to fourth pore members 151 to 154 measure the size change of the pores 51 due to binding with different types of target nucleic acids from a sample branching into the first to fourth connecting conduits 141 to 144, and detect target nucleic acids.

Here, since the probe linkers 70 are not provided on one of the first to fourth pore members 151 to 154, the pore member may be used as a negative reference channel in which the pores 51 are always open regardless of amplification of nucleic acids. Alternatively, the probe linkers 70 provided on one of the first to fourth pore members 151 to 154 may be formed so that nucleic acid amplification occurs regardless of the presence of a target nucleic acid, and thus the pore member may be used as a positive reference channel.

In addition, in the first to fourth connecting conduits 141 to 144, the electrode regions 160 including a plurality of electrodes 161 and 162 facing each other with the first to fourth pore members 151 to 154 interposed therebetween are provided. With this configuration, sample fluidity may be provided, and the degree of clogging of the first to fourth pore members 151 to 154 may be measured.

Here, the electrode regions 160 include first electrodes 161 disposed between the sample region 20 and the first to fourth pore members 151 to 154 and provided on the inlet sides 141a to 144a of the first to fourth connecting conduits 141 to 144 connected to the first to fourth pore members 151 to 154. In addition, the electrode regions 160 include second electrodes 162 disposed between the first to fourth pore members 151 to 154 and the discharge region 30 and provided on the outlet sides 141b to 144b of the first to fourth connecting conduits 141 to 144 connected to the first to fourth pore members 151 to 154.

More specifically, the electrode regions 160 include the first electrodes 161 including a first detection electrode 161a provided in the first connecting conduit 141, a second detection electrode 161b provided in the second connecting conduit 142, a third detection electrode 161c provided in the third connecting conduit 143, and a fourth detection electrode 161d provided in the fourth connecting conduit 144. The first electrodes 161 are disposed between the sample region 20 and the pore regions 150. In addition, the electrode regions 160 include the second electrodes 162 including a fifth detection electrode 162a provided in the first connecting conduit 141, a sixth detection electrode 162b provided in the second connecting conduit 142, a seventh detection electrode 162c provided in the third connecting conduit 143, and the eighth detection electrode 162d provided in the fourth connecting conduit 144. The second electrodes 162 are disposed between the pore regions 150 and the discharge region 30.

The first and second electrodes 161 and 162 including the detection electrodes 161a to 161d and the detection electrodes 162a to 162d may accurately determine whether the pores 51 are clogged by detecting a signal change due to nucleic acid amplification for each of the first to fourth connecting conduits 141 to 144. In addition, for convenience of measurement, a modification example, in which a single first electrode 161 provided between the sample region 20 and the pore regions 150 is disposed on the inlet sides 141a to 144a of the connectors 140 and the second electrodes 162 including the detection electrodes 162a to 162d provided between the pore regions 150 and the discharge region 30 are disposed to be correspond to the first to fourth connecting conduits 141 to 144, respectively, is possible.

The first and second electrodes 161 and 162 may be formed of various conductive materials including Ag/AgCl, Au, and carbon. In addition, the first and second electrodes 161 and 162 are preferably disposed on one sides of the inner surfaces of the first to fourth connecting conduits 141 to 144 so as not to interfere with sample flow.

For reference, to accurately measure the degree of clogging of the pores 51 using the first and second electrodes 161 and 162, a bias voltage may be applied as DC or AC. At this time, the degree of clogging of the pores 51 is detected by measuring current, resistance, and impedance between the first and second electrodes 161 and 162.

In addition, although not shown in detail, like the pores 51 to 56 described above with reference to FIG. 3, the pores 51 provided in the pore members 151 to 154 are micropores penetrating in the flow direction of a sample, and may be formed in various shapes such as a circle, a triangle, a square, a star, and the like. In addition, under the condition that the volume of the pores 51 is the same, the pores 51 are preferably formed in a shape with a large internal surface area.

For reference, one embodiment and another embodiment described above show an example in which detection of nucleic acids according to current change is performed by the first electrode 61 (161) and the second electrode 62 (162) of the electrode region 60 (160) that generate a flow force by an electrophoretic force. However, a modification example in which a separate electrode for detecting nucleic acids is additionally provided in the connector 40 (140) is also possible. That is, a modification example in which the electrode region 60 (160) additionally inserts electrodes in the vicinity of the pore region 40 (140) and the electrodes for measuring an electrical signal change and generating a flow force by an electrophoretic force are individually configured is also possible.

According to the present disclosure having the above configuration, a pore region having pores provided in a sample flow path between a sample region and a discharge region is provided with probe linkers to induce clogging of the pores and detect a target nucleic acid through an electrode region, thereby enabling nucleic acid detection with a simple structure. In particular, by placing electrodes so that a pore region is located between the electrodes and measuring the electrical resistance or impedance of a conductive sample fluid, a minute electrical change signal according to the degree of clogging of the pores can be measured, thereby increasing the detection accuracy of a target nucleic acid.

In addition, by temporally measuring the clogging process of the pores, the secondary effect of measuring amplification and reaction process can be obtained.

Although the present disclosure has been described above with reference to the embodiments of the present disclosure, those skilled in the art may variously modify and change the present disclosure without departing from the spirit and scope of the present disclosure as set forth in the claims below.

DESCRIPTION OF SYMBOLS

1: MICROFLUIDIC APPARATUS FOR DETECTING NUCLEIC ACIDS
10: BODY
20: SAMPLE REGION
30: DISCHARGE REGION
40, 140: CONNECTOR
50, 150: PORE REGION
60, 160: ELECTRODE REGION

What is claimed is:

1. A microfluidic apparatus for detecting nucleic acids, comprising:
   a body;
   a sample part provided on a first side of the body wherein a sample containing a target nucleic acid to be detected is injected into the sample part;
   a discharge part provided on a second side of the body and spaced apart from the sample part and the discharge part is configured to discharge the sample in which the target nucleic acid has been detected;
   a connector connecting the sample part and the discharge part to each other to provide a flow path through which the sample flows;
   a pore part provided inside the connector, having at least one pore, and configured to induce clogging of the at least one pore through amplification of the target nucleic acid contained in the sample; and
   an electrode part for determining whether the target nucleic acid is amplified by measuring an amount of change in an electrical signal of the sample passing through the pore part,
   wherein probe linkers that bind to and amplify the target nucleic acid are provided in the pore part,
   wherein the at least one pore penetrates in a flow direction of the sample from the sample part toward the discharge part,
   wherein the electrode part includes a first electrode provided at the connector between the sample part and the pore part, provided at one side of an inner surface of the connector and in contact with the sample within the connector, and a second electrode provided at one side of the inner surface of the connector between the pore part and the discharge part and in contact with the sample within the connector,
   wherein the first and second electrodes detect the target nucleic acid by measuring a degree of clogging of the at least one pore due to binding between the target nucleic acid and the probe linkers by measuring the amount of electrical signal change caused by the sample passing through the pore part, and
   wherein the sample flows from the sample part to the discharge part through an electrophoretic force generated by the first and second electrodes.

2. The microfluidic apparatus according to claim 1, wherein the body comprises upper and lower bodies that are laminated on each other.

3. The microfluidic apparatus according to claim 1, wherein the sample part and the discharge part each comprise a chamber, and the connector comprises a connecting conduit having an inlet connected to the sample part and an outlet connected to the discharge part.

4. The microfluidic apparatus according to claim 1, wherein the pore part is provided inside the connector so that the pore part is closer to the sample part than the discharge part.

5. The microfluidic apparatus according to claim 1, wherein the probe linkers comprises a coating member applied to a surface of the pore part, a primer fixed to the coating member, and a template bound to the primer.

6. The microfluidic apparatus according to claim 1, wherein a stirrer for stirring the sample is provided inside the sample part; and the stirrer stirs the sample for a preset stirring time, and then discharges the sample to the connector, wherein stirring time is variable.

7. The microfluidic apparatus according to claim 1, wherein a heating means for amplifying a binding force between the target nucleic acid and the probe linkers by heating the sample for a preset heating time is provided inside the sample part.

8. The microfluidic apparatus according to claim 1, wherein the first and second electrodes are provided on one side of the inner surface of the connector, and a direct current voltage or an alternating current voltage is applied to the first and second electrodes.

9. The microfluidic apparatus according to claim 1, wherein an additive for increasing fluidity of the sample is in the sample part, and the additive comprises ions that increase conductivity.

10. The microfluidic apparatus according to claim 1, configured to allow the sample to flow from the sample part to the discharge part by a flow force generated by at least one of negative pressure between the sample part and the discharge part, gravity according to an inclined shape of the body inclined from the sample part toward the discharge part, and a water head difference between the sample part containing the sample and the discharge part.

11. The microfluidic apparatus according to claim 10, configure to allow oil to be injected into the sample injected into the sample part to block an upper surface of the sample from outside to increase the gravity or the water head difference.

12. The microfluidic apparatus according to claim 1, wherein the connector comprises a plurality of connecting conduits each independently connecting the sample part and the discharge part, and
   the pore part comprises a plurality of pore members respectively corresponding to the plurality of connecting conduits.

13. The microfluidic apparatus according to claim 12, wherein the probe linkers provided in each of the plurality of pore members are different or the same, and a size of at least one pore provided in each of the plurality of pore members is different or the same.

14. The microfluidic apparatus according to claim 12, wherein the probe linkers are not provided on any at least one of the plurality of pore members, and the at least one of the plurality of pore members is a negative reference channel in which the at least one pore is always open regardless of amplification of a target nucleic acid, or
   the probe linkers are formed on the at least one of the plurality of pore members so that amplification occurs regardless of presence or absence of the target nucleic acid, and the at least one of the plurality of pore members is a positive reference channel.

15. The microfluidic apparatus according to claim 12, wherein a first electrode is provided at an inlet of each of the plurality of connecting conduits respectively connected to the plurality of pore members and respectively positioned between the sample part and the plurality of pore members, and a plurality of the second electrodes is provided at an outlet of each of the plurality connecting conduits respectively connected to the plurality of pore members and respectively positioned between the plurality of pore members and the discharge part.

16. A microfluidic apparatus for detecting nucleic acids, comprising:

a sample part into which a sample containing a target nucleic acid to be detected is injected;

a discharge part spaced apart from the sample part and configured to discharge the sample;

a connector providing a sample flow path between and connecting the sample part to the discharge part;

a pore part having at least one pore, provided in the flow path, and provided with probe linkers that bind to and amplify the target nucleic acid to induce clogging of the at least one pore; and an electrode part for measuring whether the target nucleic acid is amplified through the pore part by measuring an amount of electrical signal change of the sample before and after passing through the pore part, and a body having the sample part, the discharge part, the connector, the pore part, and the electrode part, wherein the at least one pore penetrates in a flow direction of the sample from the sample part toward the discharge part, wherein the electrode part includes a first electrode provided at the connector between the sample part and the pore part, provided at one side of an inner surface of the connector and in contact with the sample within the connector, and a second electrode provided at one side of the inner surface of the connector between the pore part and the discharge part and in contact with the sample within the connector, wherein the first and second electrodes detect the target nucleic acid by measuring a degree of clogging of the at least one pore due to binding between the target nucleic acid and the probe linkers by measuring the amount of electrical signal change caused by the sample passing through the pore part, wherein the sample flows from the sample part to the discharge part through an electrophoretic force generated by the first and second electrodes, and wherein the sample part and the discharge part comprise a chamber in the body.

\* \* \* \* \*